United States Patent
Chen et al.

(10) Patent No.: US 6,846,106 B1
(45) Date of Patent: Jan. 25, 2005

(54) FINGER TEMPERATURE DETECTING DEVICE WITH RELAXATION INDICATION

(76) Inventors: Mei-Yen Chen, 21th Floor, No. 2, Lane 20, Chorng-Shyue Road, Tainan City (TW); Fong-Lin Jang, 21th Floor, No. 2, Lane 20, Chorng-Shyue Road, Tainan City (TW)

( * ) Notice: Subject to any disclaimer, the term of this patent is extended or adjusted under 35 U.S.C. 154(b) by 0 days.

(21) Appl. No.: 10/765,937

(22) Filed: Jan. 29, 2004

(51) Int. Cl.[7] .......................... G01K 1/14; G01K 1/16; G01K 7/22; G08B 23/00; A61B 5/00
(52) U.S. Cl. .................. 374/141; 374/183; 374/121; 374/102; 600/474; 600/549; 600/27; 128/905; 63/1.13; 340/573.1; 340/407.1
(58) Field of Search ........................ 374/141, 183, 374/121, 208, 102, 107, 45; 600/474, 549, 504, 26–28; 128/905; 63/1.13, 15; 340/573.1, 407.1

(56) References Cited

U.S. PATENT DOCUMENTS

| | | | |
|---|---|---|---|
| 4,407,295 A | * | 10/1983 | Steuer et al. ............... 600/549 |
| 4,509,531 A | * | 4/1985 | Ward .......................... 600/549 |
| 5,771,261 A | * | 6/1998 | Anbar .......................... 374/45 |
| 5,813,766 A | * | 9/1998 | Chen .......................... 374/141 |
| 5,964,701 A | * | 10/1999 | Asada et al. ................ 600/300 |
| 2003/0234726 A1 | * | 12/2003 | Chen et al. .............. 340/573.1 |

* cited by examiner

Primary Examiner—Diego Gutierrez
Assistant Examiner—Stanley J. Pruchnic, Jr.
(74) Attorney, Agent, or Firm—Rosenberg, Klein & Lee

(57) ABSTRACT

A finger temperature detecting device includes a carrier, a finger-attachment member extending from the carrier, a temperature sensor mounted in the carrier for detecting skin temperature of the finger of the wearer, and means of informing the wearer when a temperature value detected by the temperature sensor is larger than the precedent reading. The finger-attachment member is wearable on a finger of a wearer and allows adjustment in wearing tightness to securely retain appropriate attachment of the temperature sensor to a fixed survey area of finger surface. In another embodiment, a seat extends from the carrier for receiving the temperature sensor.

8 Claims, 6 Drawing Sheets

FINGER TEMPERATURE DETECTING DEVICE WITH RELAXATION INDICATION

BACKGROUND OF THE INVENTION

1. Field of the Invention

The present invention relates to a finger temperature detecting device with relaxation indication. In particular, the present invention relates to a finger temperature detecting device providing an index to relaxation of the wearer.

2. Description of the Related Art

Modern people are facing much more stress than ever due to rapid economic development. Psychiatric problems, such as insomnia, neuroses, psychoses, and psychosomatic disorders (including migraine, peptic ulcer, tension headache, etc.) become more and more common among people. According to statistic data, there are about 5 to 15 percents of adults suffering from such problems.

The physical body and the mind of the human are interactive; namely, physical diseases may cause mental disorders, and mental discomfort may have adverse influence on physical health. Physical and/or mental disorder may develop when one is encountering unbearable stress. This is because muscular tension and/or dysfunction of the nervous systems, immune systems, and hormone systems may be caused via the effect of neurological pathways when the brain senses the unbearable stress.

The symptoms of anxiety caused by autonomic nervous system dysfunction may be palpitation, dyspnea, chest tightness, dizziness, headache, dry mouth, gastrointestinal upset, diarrhea, constipation, polyuria, sweating, tremor, cold extremities, etc. Among these, cold limbs are due to vasoconstriction caused by excessive sympathetic tone. And clinically finger temperature has been used as a general sensitive index to monitor one's sympathetic tone and to see if one is relaxed or not. More specifically, if one is relaxed, his or her arteriolae will be dilated and his or her surface of fingers will be warmer, as more heat is transmitted to the skin. On the other hand, if one is anxious and tense, the arteriolae will be constricted and his or her surface of fingers will be cooler, as less heat is transmitted to the skin.

In clinical practice, a medical doctor may instruct a patient how to do muscle relaxation with the help of a biofeedback machine. The temperature biofeedback machine includes a sensor in contact with a patient's skin to detect the surface temperature. The measured temperature values are converted into electronic signals that are then presented on a monitor to tell the patient if he or she is in a relaxed condition. By this way, medical doctors can confirm that their patients are practicing muscle relaxation in the right way. In the past, the sensor of the biofeedback machine is fixed by a tape or a strap to the finger, which may cause local compression to the finger and thus interfere with the circulation. So the temperature readings may be diverted and the results unreliable.

U.S. Pat. No. 5,813,766 discloses a finger temperature indicating ring that can be put on a finger of the wearer at any time to serve as an auxiliary medical instrument to effectively sense and indicate the wearer's finger temperature which reflects a physical and/or mental relaxing condition of the wearer, so as to help the wearer, either a physchiatric patient or a general user, to timely control or adjust his or her emotional condition. The finger temperature indicating ring includes a ring body having two channels, a thermal conductive rod buried in one of the channels, and a discharge rod buried in the other channel. The finger temperature indicating ring worn on the wearer's finger may slide and thus result in unstable examination, as the wearer could not adjust the tightness of the finger temperature indicating ring. Further, the thermal conductive rod and the discharge rod respectively buried in the channels may cause erroneous examination, as the heat at the survey area of the finger could not be effectively dissipated even though the finger temperature drops.

SUMMARY OF THE INVENTION

In accordance with an aspect of the invention, a finger temperature detecting device comprises a carrier including a compartment defined therein, a finger-attachment member extending from the carrier, the finger-attachment member being wearable on a finger of a wearer, a seat extending from the perimeter of the carrier, and a circuit board mounted in the compartment of the carrier. The seat includes an opening portion facing the finger of the wearer. A temperature sensor is mounted in the opening portion of the seat for detecting temperature of the finger of the wearer. The circuit board includes a calculating unit electrically connected to the temperature sensor and a signaling means electrically connected to the calculating unit. The calculating unit sends a signal to activate the signaling means to inform the wearer when a temperature value detected by the temperature sensor is larger than the precedent reading.

In accordance with another aspect of the present invention, a finger temperature detecting device comprises a carrier including a compartment defined therein, a finger-attachment member extending from the carrier, the finger-attachment member being wearable on a finger of a wearer, a seat extending from the carrier, a temperature sensor mounted in the seat for detecting temperature of the finger of the wearer, and means for signaling the wearer when a temperature value detected by the temperature sensor is larger than a precedent reading.

In accordance with a further aspect of the present invention, a finger temperature detecting device includes a carrier, a finger-attachment member extending from the carrier, a temperature sensor mounted in the carrier for detecting temperature of the finger of the wearer, and means for signaling the wearer when the temperature value is larger than the precedent reading.

The finger-attachment member is wearable on a finger of the wearer and allows adjustment in wearing tightness to reassure the attachment of this component to the finger of the wearer.

In an embodiment of the invention, the finger-attachment member is elastomeric and has an end, and a gap is defined between the end of the finger-attachment member and the carrier. The carrier includes a compartment, a circuit board mounted in the compartment, a calculating unit electrically connected to the temperature sensor, and a signaling means electrically connected to the calculating unit. The calculating unit sends a signal to activate the signaling means to inform the wearer when a temperature value detected by the temperature sensor is larger than the precedent reading.

The temperature sensor can be a thermistor in contact with dorsum of the finger of the wearer when the finger temperature detecting device is worn on the finger of the wearer. The temperature sensor is coated by a soft, non-toxic, and highly transcalent material. Alternatively, the temperature sensor can be a non-contact infrared sensor.

A seat extends from the perimeter of the carrier. A metal jacket is mounted in the seat. A thermal insulating member is mounted to an end of the metal jacket. The temperature sensor is mounted in the seat and exposed via the end of the thermal insulating member, avoiding over-conduction of heat by the metal jacket.

Preferably, the temperature sensor is in an appropriate position so that the heat can be dissipated effectively and the sensor can be fixed firmly without too much local compression to the finger. As there is no sliding of the instrument, the temperature of only one fixed area of the finger is monitored, which is rather important in biofeedback instrumentation.

A panel is mounted to the carrier and seals the compartment of the carrier. A plurality of functional buttons associated with the calculating unit are mounted on the panel.

Data relevant to the detected finger temperature can be sent to a remote receiver or server.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
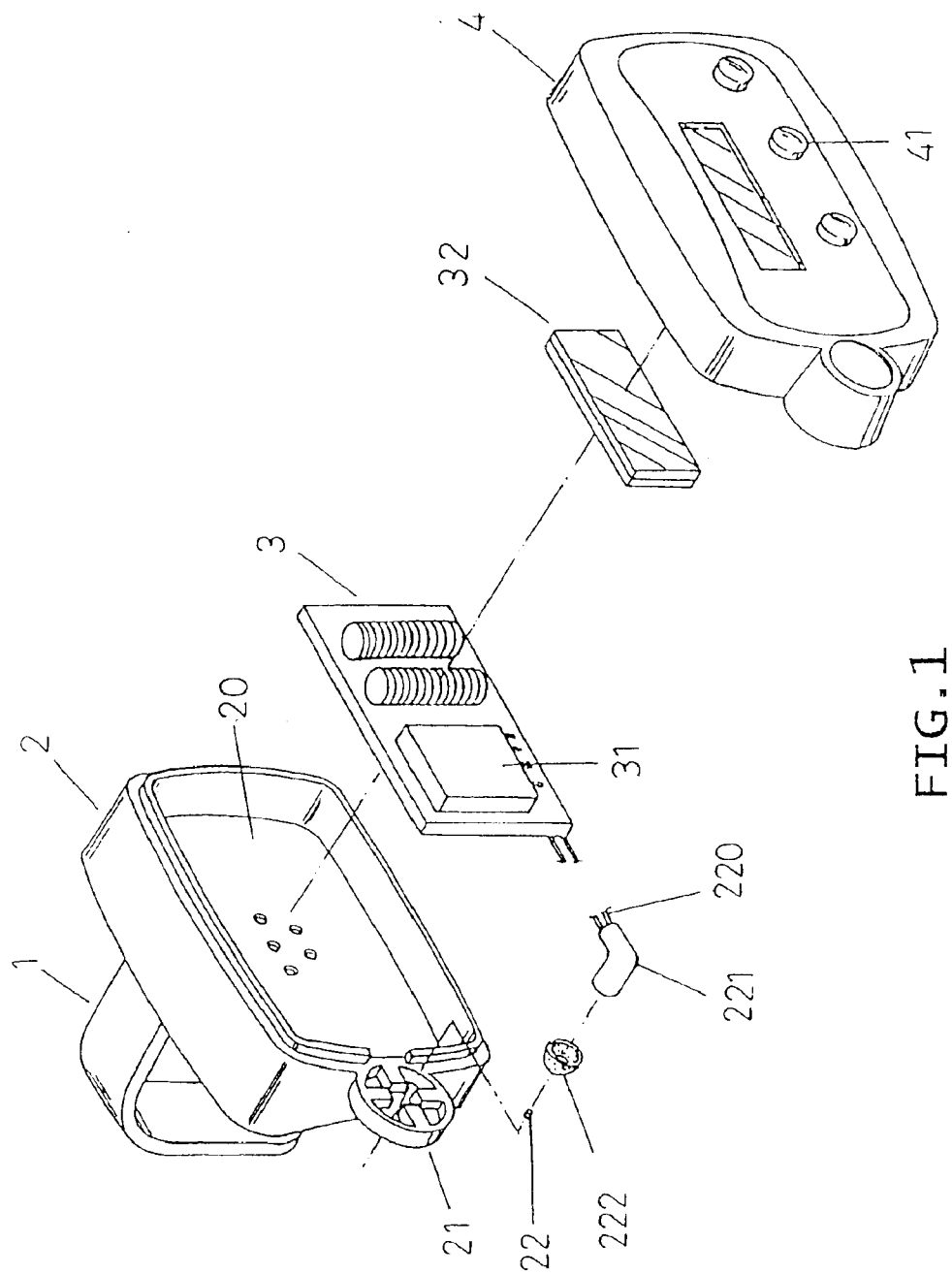
FIG. 1 is an exploded perspective view of a finger temperature detecting device in accordance with the present invention.
Figure 3:
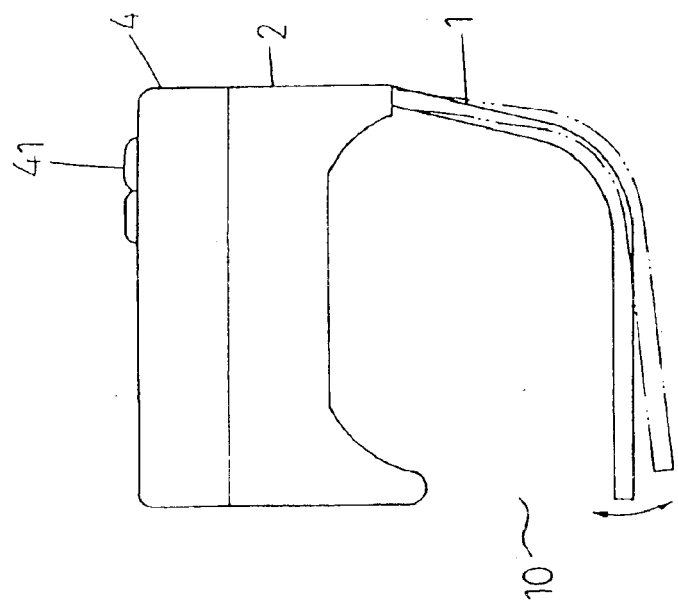
FIG. 3 is a side view of the finger temperature detecting device in accordance with the present invention.
Figure 2:
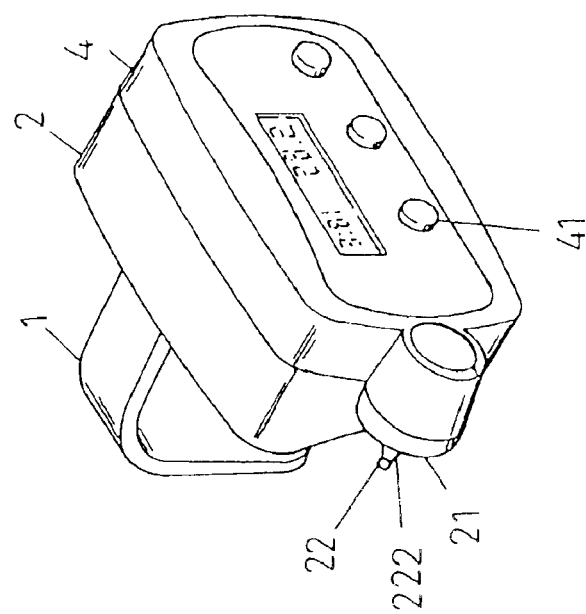
FIG. 2 is a perspective view of the finger temperature detecting device in accordance with the present invention.

Referring to FIGS. 1 through 3, a finger temperature detecting ring in accordance with the present invention generally comprises a finger-attachment member 1, a carrier 2, a circuit board 3, and a panel 4. The finger-attachment member 1 is attached to a side of the carrier 2 and can be worn on a finger of a wearer. The finger-attachment member 1 is elastomeric and may deform in response to the size of the wearer's finger to allow adjustment in the wearing tightness in response to the size of the finger of the wearer when the finger temperature detecting device is worn on the finger of the wearer (see FIG. 2). In an embodiment of the invention, the finger-attachment member 1 is substantially L-shaped and has an end, with a gap 10 defined between the end of the end of the finger-attachment member 1 and the carrier 2.

The carrier 2 includes a compartment 20 for receiving the circuit board 3. A seat 21 extends outward from a perimeter of the carrier 2. A temperature sensor 22 is mounted to an opening portion (not labeled) of the seat 21. When the finger temperature indicating device is worn on the finger of the wearer, the temperature sensor 22 is in slight contact with the back of the finger (which is a preferred finger temperature detecting portion according to the medical principle), and the temperature sensor 22 is thus retained in place. The temperature sensor 22 may be coated by a soft, non-toxic, and highly transcalent material.

A metal jacket 221 is mounted to the seat 21 and receives a conductive wire 220. The metal jacket 221 carries and protects the temperature sensor 22. A thermal insulating member 222 is mounted to an end of the metal jacket 221, with the temperature sensor 22 being exposed via the end of the thermal insulating member 222. This avoids adverse affect to the temperature-measuring accuracy resulting from over-conduction of heat by the metal jacket 221.

The circuit board 3 mounted in the compartment 20 of the carrier 2 includes a calculating unit 31 and a signaling means 32 electrically connected to the calculating unit 31. A change in the finger temperature causes a change, e.g., a change in the resistance of the temperature sensor 22. The panel 4 is attached to the carrier 2 and seals the compartment 20. A plurality of functional buttons 41 associated with the calculating unit 31 are provided on the panel 4.

Figure 4:
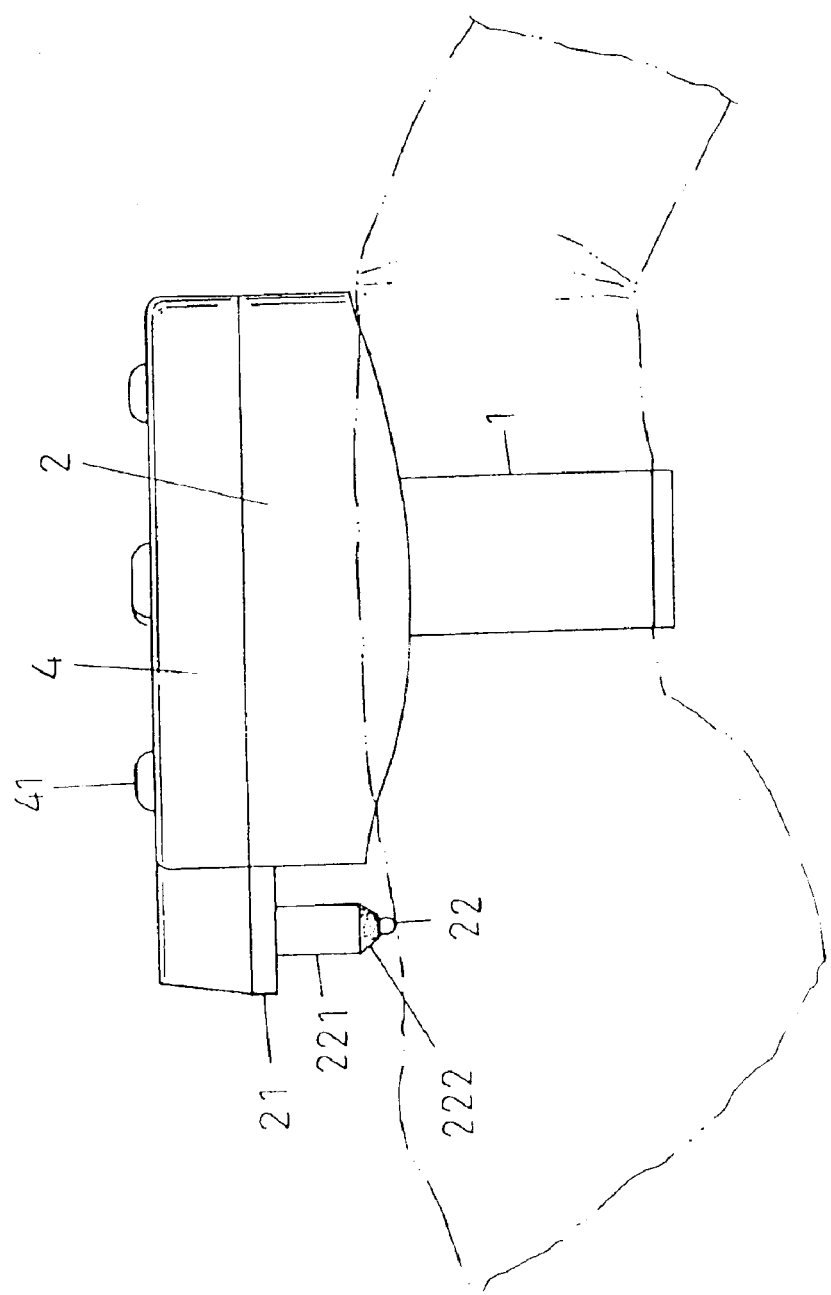
FIG. 4 is another side view illustrating use of the finger temperature detecting device.
Figure 5:
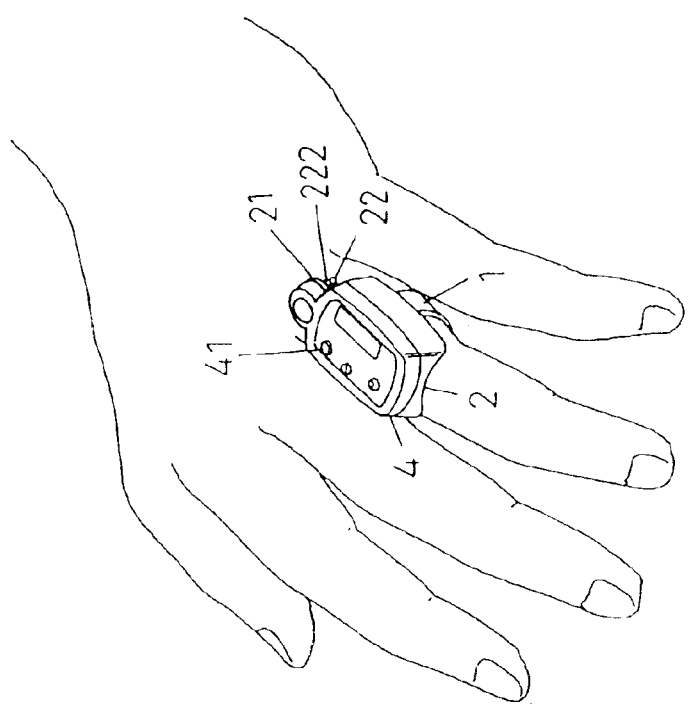
FIG. 5 is a schematic perspective view illustrating use of the finger temperature detecting device.
Figure 6:
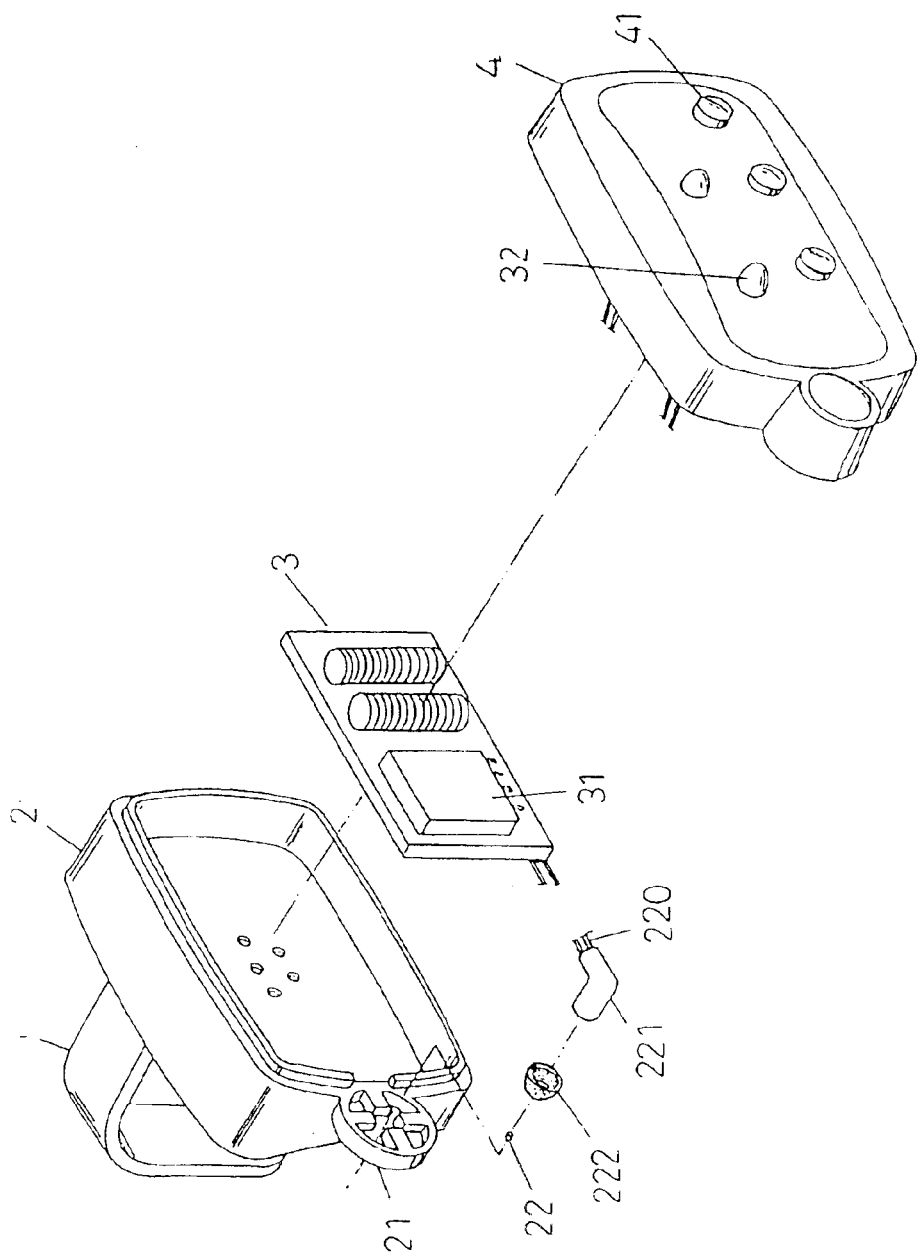
FIG. 6 is an exploded perspective view of a modified embodiment of the finger temperature detecting device in accordance with the present invention.

Referring to FIGS. 4 and 5, when the finger temperature detecting device is worn on the finger of the wearer, the temperature sensor 22 is in contact with the skin of the finger. Thus, the electronic variation after temperature change of the finger surface is transmitted via the conductive wire 22 to the calculating unit 31 of the circuit board 3, thereby detecting the finger temperature. When the finger temperature value is larger than the precedent reading (i.e., the wearer is in a relaxed state), a signal is sent to actuate the signaling means 32 (such as a vibration motor, a LED, a buzzer, a liquid crystal display, etc.) to inform the wearer of the relaxation. In this embodiment, the signaling means 32 is a liquid crystal display that shows the detected finger temperature value and/or sign when the finger temperature value is larger than the precedent reading. In another embodiment shown in FIG. 6, the signaling means 32 is a light-emitting diode (LED) that emits light when the finger temperature value is larger than the precedent reading. The signaling means 32 is actuated when relaxation is indicated. In a case that the signaling means 32 is an LED in FIG. 6, relaxation may be indicated by changing the color of the light emitted by the LED. Besides, the detected finger temperature value can be transferred via computer network or a wireless communication system to a remote server for further information processing. And the doctor in charge of the patient wearing the finger temperature detecting device may remotely receive the information and respond properly.

Figure 7:
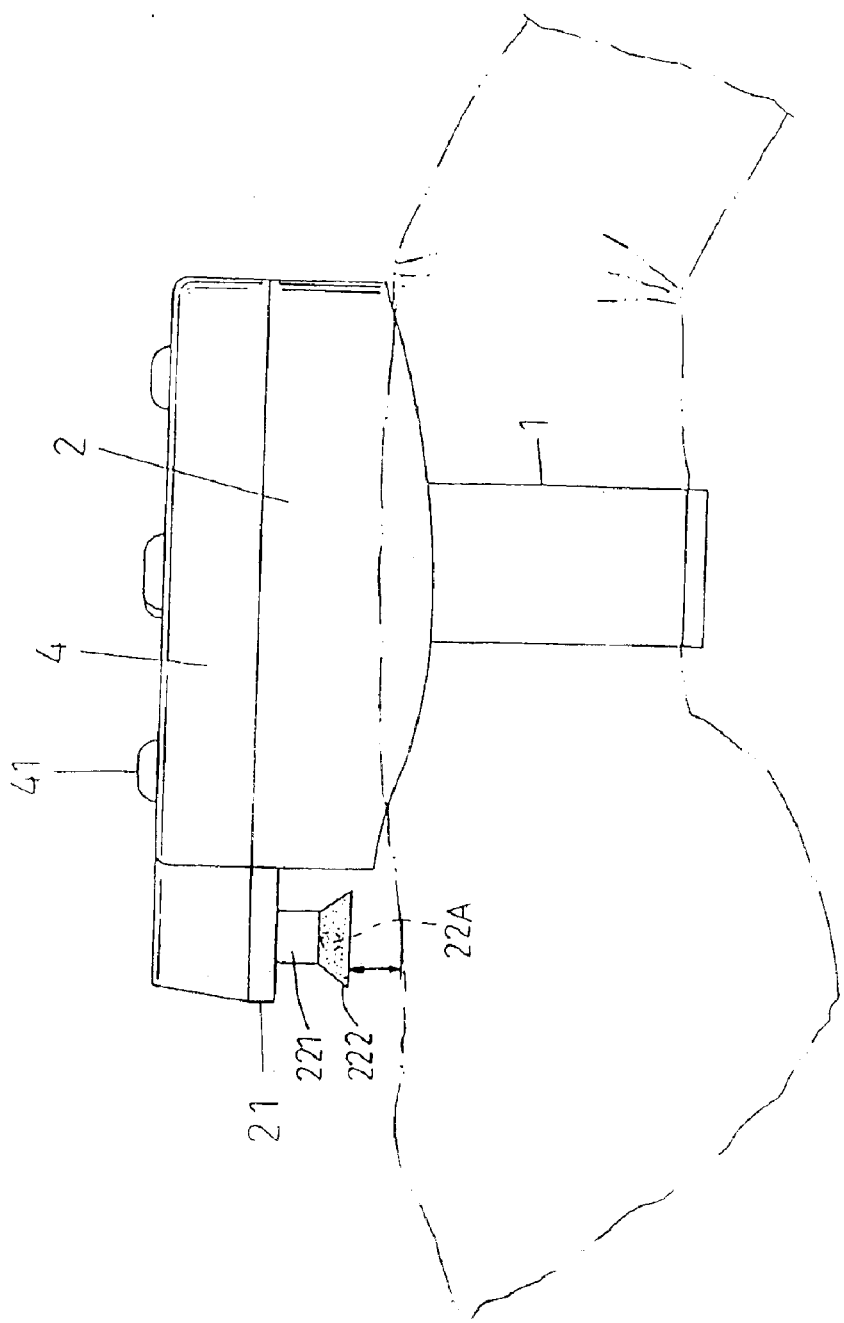
FIG. 7 is a schematic side view illustrating use of another modified embodiment of the finger temperature detecting device in according to the present invention.

The contact type temperature sensor 22 is suitable for one whose finger hair is dense and long. If the wearer's finger hair is sparse and short, the non-contact infrared temperature sensor 22A (see FIG. 7) may be used. The mechanism is: the higher the finger temperature is, the more infrared energy will be emitted. The infrared energy radiated by the finger is detected by the infrared sensor 22A and converted into an electronic signal by the calculating unit 31. The electronic signal is then amplified and display as a temperature reading.

When the finger temperature detecting device is worn on the finger of the wearer, the local blood circulation will not be adversely affected. Thus, the temperature detection is accurate. Further, the wearing tightness of the finger temperature detecting device can be adjusted (see FIG. 3) so the temperature sensor 22, 22A can get a good position to the finger area to be detected. Sliding of the temperature sensor is avoided, providing a stable state for temperature detection. Further, the temperature sensor 22, 22A is located outside the carrier 2, allowing heat dissipation and obtaining accurate data.

Although the invention has been explained in relation to its preferred embodiments, it is to be understood that many other possible modifications and variations can be made without departing from the scope of the invention as hereinafter claimed.

What is claimed is:

1. A finger temperature detecting device comprising:

a carrier including a compartment defined therein;

a finger-attachment member extending from the carrier, the finger-attachment member being wearable on a finger of a wearer;

a seat extending from a perimeter of the carrier, the seat including an opening portion facing the finger of the wearer;

a temperature sensor mounted in the opening portion of the seat directed toward the finger for detecting the temperature of the finger of the wearer; and a circuit board mounted in the compartment of the carrier, the circuit board including a calculating unit electrically connected to the temperature sensor and a signaling means electrically connected to the calculating unit, the calculating unit sending a signal to activate the signaling means to inform the wearer when a temperature value detected by the temperature sensor is larger than a preceding finger temperature value.

2. The finger temperature detecting device as claimed in claim 1, wherein the finger-attachment member is elastomeric and has an end, a gap being defined between the end of the finger-attachment member and the carrier.

3. The finger temperature detecting device as claimed in claim 1, wherein the temperature sensor is coated by a soft, non-toxic, and highly transcalent material.

4. The finger temperature detecting device as claimed in claim 1, wherein the temperature sensor is a contact type sensor in contact with the finger of the wearer when the finger temperature detecting device is worn on the finger of the wearer.

5. The finger temperature detecting device as claimed in claim 1, wherein the temperature sensor is a non-contact infrared sensor.

6. The finger temperature detecting device as claimed in claim 1, further including a metal jacket mounted in the seat, a thermal insulating member being mounted to an end of the metal jacket, the temperature sensor being exposed via the end of the thermal insulating member, thereby avoiding over-conduction of heat by the metal jacket.

7. The finger temperature detecting device as claimed in claim 1, further including a panel mounted to the carrier and sealing the compartment of the carrier, a plurality of functional buttons associated with the calculating unit being mounted on the panel.

8. The finger temperature detecting device as claimed in claim 1, further including means for sending data relevant to detected finger temperature to a remote receiver.

* * * * *